(12) United States Patent
Wheatley (10) Patent No.: US 9,662,009 B2
(45) Date of Patent: May 30, 2017

(54) IMAGING PROBES AND ASSOCIATED DEVICES, AND SYSTEMS UTILIZING FERROFLUID-IMPREGNATED ACTUATORS

(71) Applicant: Novartis AG, Basel (CH)

(72) Inventor: Barry L. Wheatley, Oceanside, CA (US)

(73) Assignee: NOVARTIS AG, Basel (CH)

( * ) Notice: Subject to any disclaimer, the term of this patent is extended or adjusted under 35 U.S.C. 154(b) by 665 days.

(21) Appl. No.: 14/137,102

(22) Filed: Dec. 20, 2013

(65) Prior Publication Data

US 2015/0173603 A1    Jun. 25, 2015

(51) Int. Cl.

| | |
|---|---|
| A61B 3/10 | (2006.01) |
| G02B 26/10 | (2006.01) |
| A61B 3/12 | (2006.01) |
| G02B 6/36 | (2006.01) |
| G01B 9/02 | (2006.01) |
| G02B 23/24 | (2006.01) |
| G02B 23/26 | (2006.01) |
| A61B 5/00 | (2006.01) |
| G02B 6/35 | (2006.01) |

(52) U.S. Cl.
CPC ............ *A61B 3/102* (2013.01); *A61B 3/1208* (2013.01); *G01B 9/0205* (2013.01); *G01B 9/02091* (2013.01); *G02B 6/3624* (2013.01); *G02B 23/2469* (2013.01); *G02B 23/26* (2013.01); *G02B 26/103* (2013.01); *A61B 5/0084* (2013.01); *G02B 6/3572* (2013.01)

(58) Field of Classification Search
CPC ..... A61B 3/102; A61B 3/1208; A61B 5/0084; G01B 9/0205; G01B 9/02091; G02B 23/2469; G02B 23/26; G02B 26/103; G02B 6/3572; G02B 6/3624
See application file for complete search history.

(56) References Cited

U.S. PATENT DOCUMENTS

| | | |
|---|---|---|
| 4,384,761 A | 5/1983 | Brady et al. |
| 6,553,161 B1 | 4/2003 | Upton |
| 2013/0178933 A1 | 7/2013 | Serrano Olmedo et al. |

FOREIGN PATENT DOCUMENTS

WO    WO 2012/166116    12/2012

OTHER PUBLICATIONS

International Search Report and Written Opinion issued for PCT/US2014/069144 dated Feb. 23, 2015, 12 pgs.
Ding et al. in "Ferrofluid-Impregnated Paper Actuators," Journal of Microelectricalmechanical Systems 20.1 (2011): 59-64.

*Primary Examiner* — Ruth S Smith
(74) *Attorney, Agent, or Firm* — Joseph Weatherbee (57) ABSTRACT

Devices, systems, and methods that utilize a ferrofluid-impregnated medium to impart motion to an optical fiber positioned within an imaging probe are provided. In some embodiments, an ophthalmic imaging probe can include a housing having a proximal portion and a distal portion; an optical fiber positioned within the housing, the optical fiber configured to receive an imaging light from an imaging light source and guide the imaging light to an optical element positioned within the distal portion of the housing; and an actuator system configured to impart motion to the optical fiber, the actuator system including a ferrofluid-impregnated medium (FIM) and an electrically energizable coil positioned within the housing.

18 Claims, 5 Drawing Sheets

Fig. 1

Fig. 9

IMAGING PROBES AND ASSOCIATED DEVICES, AND SYSTEMS UTILIZING FERROFLUID-IMPREGNATED ACTUATORS

TECHNICAL FIELD

Embodiments disclosed herein are related to devices, systems, and methods for scanning tissue with an optical coherence tomography (OCT) probe, and more particularly, to devices, systems, and methods that utilize an OCT probe having a displaceable fiber for ophthalmic imaging.

BACKGROUND

Optical Coherence Tomography (OCT) systems are used to capture and generate images of patient tissue layers. These systems often include OCT probes that can invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from sub-surface features of the tissue and is collected through the same probe. Most of the light is not reflected but, rather, diffusely scatters at large angles. In conventional imaging, this diffusely scattered light contributes background noise that obscures an image. However, in OCT, a technique called interferometry records the optical path lengths of received photons, and provides data that rejects most of the photons that scatter multiple times before detection. This results in images that are clearer and that extend in the depth of the tissue.

The OCT probes often include a projecting cannula that can invasively penetrate patient tissue. The probe scans tissue by refracting the optical light beam through a lens disposed at an end of the cannula. A scan can include moving an optical fiber back and forth within the cannula to direct the light beam through the lens and at the tissue at different angles. The length and small diameter of the cannula make it difficult to move the fiber back and forth within the cannula. Further, the small amount of available space within the probe limits the types of actuators that can be utilized. Further still, the OCT probes and associated systems must be capable of being manufactured in a cost-effective manner, which includes the ability to make the probe as a disposable, one-time use device in some implementations.

Accordingly, there is a need for improved devices, systems, and methods that utilize an OCT probe having a displaceable fiber for ophthalmic imaging, including ophthalmic OCT probes that address one or more of the needs discussed above.

SUMMARY

Embodiments disclosed herein are related to devices, systems, and methods that utilize a ferrofluid-impregnated medium to impart motion to an optical fiber positioned within an imaging probe.

Consistent with some embodiments, an ophthalmic imaging apparatus is provided. The ophthalmic imaging apparatus can include an optical probe having a handle sized and shaped for handheld grasping by a user and a cannula coupled to the handle. The cannula can be sized and shaped for insertion into an eye to be treated. An optical fiber can be positioned within the optical probe. The optical fiber can be configured to receive an imaging light from an imaging light source and guide the imaging light to an optical element positioned within the cannula of the optical probe. An actuator system can be configured to impart motion to the optical fiber. The actuator system can include a ferrofluid-impregnated medium (FIM) and an electrically energizable coil positioned within the optical probe.

Consistent with some embodiments, an ophthalmic imaging system comprises an imaging light source, configured to generate an imaging light; and a probe, including a handle, sized and shaped for handheld grasping by a user; a cannula, coupled to the handle, the cannula sized and shaped for insertion into an eye to be treated; an optical fiber, positioned partially within the probe, in optical communication with the imaging light source to guide the imaging light to an optical element positioned in a distal region of the cannula; and an actuator system configured to impart motion to the optical fiber, the actuator system including a ferrofluid-impregnated medium (FIM) and an electrically energizable coil positioned within the probe.

Consistent with some embodiments, a method of ophthalmic imaging is provided. The method can include energizing an electrically energizable coil positioned within a housing of ophthalmic probe to deflect a ferrofluid-impregnated medium (FIM) positioned within the housing adjacent to the electrically energizable coil, wherein deflection of the FIM causes an optical fiber coupled to the FIM to scan an imaging light passing through the optical fiber across an optical element positioned within a distal portion of the housing.

Additional aspects, features, and advantages of the present disclosure will become apparent from the following detailed description.

BRIEF DESCRIPTION OF THE DRAWINGS

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The probe can include a cannula configured to invasively penetrate patient tissue, such as the globe of an eye. The cannula can house a lens and an optical fiber. The fiber directs light through the lens and captures reflected light that passes back through the lens. To obtain a scan of an area or a line of tissue, rather than merely a point, the fiber can be moved within the cannula relative to the lens to cause the light emerging from the lens to scan across the desired pattern. Because the cannula that penetrates the patient tissue is desirably small in cross-section, moving the fiber within the cannula is difficult. The small amount of available space within the probe limits the types of actuators that can be utilized to impart movement to the fiber. In some instances it is desirable to manufacture the probe, or at least a portion thereof, as a disposable component, which requires product designs having cost-effective manufacturing techniques.

Exemplary aspects described herein utilize a technique of moving at least a distal end of the fiber within the cannula using an actuator system positioned within the probe that overcomes one or more of the problems or limitations of previous approaches. The actuator system can include a ferrofluid-impregnated medium (FIM) and an electrically energizable coil. The FIM and coil can be positioned outside the cannula, such as in a proximal portion of a housing of the probe, or inside the cannula. The distal end of the fiber can be moved by selectively electrically activating the coil to cause the FIM to be either urged towards or away from the coil as a result of the electromagnetic field generated by activating the coil. The fiber can be coupled to the FIM such that the movement of the FIM results in a corresponding movement of the distal end of the fiber. As a result, embodiments of the present disclosure (1) can be configured for use within the limited space available within an OCT probe, (2) can amplify the motion of the distal end of the fiber relative to the motion of the FIM, (3) can avoid the need for an actuator system that relies upon an interaction of mechanical components that can require very precise manufacturing tolerances, be difficult to assemble, and have a tendency to break at the sizes necessary for use in an OCT probe (4) can impart repeatable motion to the optical fiber of the OCT probe suitable for optical scanning, and (5) can be manufactured in a cost-effective manner.

Figure 1:
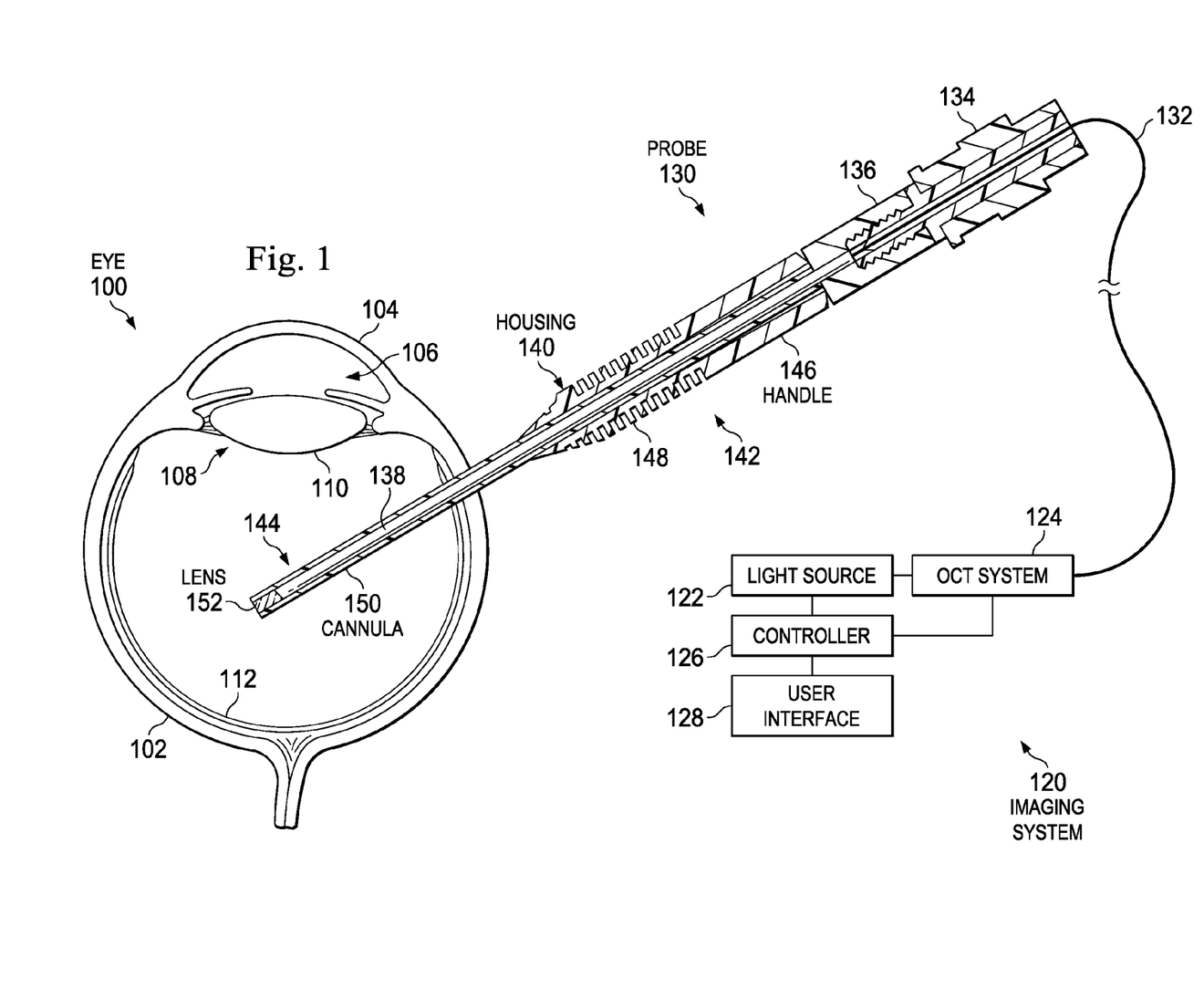
FIG. 1 is a diagrammatic schematic view of an eye under treatment and an exemplary OCT imaging system.

FIG. 1 is a diagrammatic schematic view of an arrangement illustrating aspects of the present disclosure. In particular, an eye 100 under treatment is shown. The eye 100 includes sclera 102, a cornea 104, an anterior chamber 106, and a posterior chamber 108. A capsular bag 110 is illustrated in the posterior chamber 108. The eye 100 further includes a retina 112.

An exemplary imaging system 120 is also illustrated in FIG. 1. As discussed in greater detail below, imaging system 120 is configured to image portions of the eye 100, such as the retina 112. The imaging system 120 can include a light source 122, an optical coherence tomography (OCT) system 124, a controller 126, a user interface 128, and a probe 130. The light source 122 is configured to provide imaging light that will be directed onto the target biological tissue by the probe 130. The light source 122 can be made up of superluminescent diodes, ultra-short pulsed lasers, or supercontinuum lasers that provide relative long wavelength light, such as between 700 nm and 1400 nm, between 900 nm and 1200 nm, or between 1000 nm and 1100 nm. Imaging light reflected from the target biological tissue and captured by the probe 130 is utilized to generate images of the target biological tissue.

The OCT system 124 is configured to split the imaging light received from the light source 122 into the imaging beam that is directed onto the target biological tissue by the probe 130 and a reference beam that can be directed onto a reference mirror. The OCT system 124 can be a spectral domain or a time domain system. The OCT system 124 is further configured to receive the imaging light reflected from the target biological tissue and captured by the probe 130. The interference pattern between the reflected imaging light and the reference beam is utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the probe 130, and for executing and performing functions and processes to carry out an OCT imaging procedure. For example, the controller 126 is configured to control an actuation system of probe 130 configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller are positioned within a console that is communicatively coupled to the user interface 128. The user interface 128 can be carried on or form part of the console. Further, the user interface 128, or at least part(s) thereof, can be separate from the console. The user interface 128 can include a display configured to present images to a user or a patient, and display tissue scanned by the probe 130 during an OCT imaging procedure. The user interface 128 can also include input devices or systems, including by way of non-limiting example, a keyboard, a mouse, a joystick, a touchscreen, dials, and buttons, among other input devices.

The probe 130 is in optical communication with OCT system 124. In that regard, the probe 130 is configured to present light from the light source 122 that passes through OCT system 124 onto the target biological tissue for the purpose of imaging the tissue. Further, the probe can be in electrical communication with the controller 126. In that regard, the controller 126 can control an actuation system of the probe 130 via electrical signals sent to the probe 130 in order to cause the actuation system to scan the imaging beam across the target biological tissue. A cable 132 can connect the probe 130 to the OCT system 124 and/or the controller 126. In that regard, cable 132 can include optical fiber(s), electrical conductor(s), insulator(s), shield(s), and/or other features configured to facilitate optical and/or electrical communication between the probe 130 and the OCT system 124 and/or the controller 126. Further, it is understood that cable 132 can include multiple, separate cables. For example, in some instances an optical cable connects the probe 130 to OCT system 124 and a separate electrical cable connects the probe 130 to controller 126.

In the illustrated embodiment, the cable 132 terminates in a connector 134 that is configured to facilitate removable coupling of the probe 130 to the cable 132. The connector 134 is configured to selectively engage with a connector 136 associated with the probe 130 to facilitate mechanical, optical, and/or electrical coupling of the probe 130 to the cable 132. For example, an optical fiber 138 extending along the length of the probe 130 is optically coupled to the OCT system 124 via the coupling of the connectors 134 and 136. The optical fiber 138 can be a single fiber or a fiber bundle. In some embodiments, the optical fiber 138 of the probe 130 extends through the cable 132, being optically coupled to the light source 122 through the OCT system 124. In the illustrated embodiment, the connector 136 is configured to threadingly engage with the connector 134. However, it is understood that any type of selective engagement feature(s) or connectors can be utilized to couple the probe 130 to the cable 132, including without limitation press fit, luer lock, threads, and combinations thereof, among other connection types. The selective engagement of the connector 136 with the connector 134 allows the entire probe 130 to be a disposable component configured for use in a single procedure, while the connector 134 and cable 132 are reusable components that can be sterilized (e.g., using autoclave procedures) and used in multiple procedures.

The probe 130 is sized and shaped to be handled by a surgeon and to protrude into a body of the patient. The probe 130 includes a housing 140 having a proximal portion 142. The proximal portion 142 of the housing 140 can be sized and shaped for handheld grasping by a user. For example, the proximal portion 142 of the housing 140 can define a handle 146. The handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the user controls the position of a distal portion 144 of the probe 130 by maneuvering the handle 146 such that the imaging light beam is directed towards the target biological tissue.

The distal portion 144 of the probe 130 can be sized and shaped for insertion into the eye 100 to be treated. In the illustrated embodiment of FIG. 1, the distal portion 144 of the probe 130 includes a cannula 150. The cannula 150 can be sized and shaped for insertion through the sclera 102 of the eye 100 to facilitate imaging of the retina 112. The cannula 150 can be integrally formed with the handle 146 as part of the housing 140. Alternatively, the cannula 150 and the handle 146 can be separate components fixedly secured to one another to form the housing 140. An optical element 152, such as a lens, can be secured within the distal end of the cannula 150. The optical element 152 is configured to focus the imaging light onto the target biological tissue, such as the retina 112. The optical element 152 can be a lens or a gradient index (GRIN) lens. Depending upon the embodiment, the gradient index may be spherical, axial, or radial. The optical element 152 can also be a spherical lens. Other lens shapes may be used.

As will be discussed in greater detail below, the optical fiber 138 is moved with respect to the optical element 152 by an actuator system disposed within the probe 130 to cause the imaging beam—as focused by the optical element 152—to scan across a portion of the target biological tissue. FIGS. 3 and 5-9 described below illustrate various exemplary embodiments of actuator systems in accordance with the present disclosure. In that regard, it is understood that the actuator systems of the present disclosure can be positioned within the handle 146, within the cannula 150, and/or combinations thereof to move the optical fiber 138 across a desired scan pattern.

The distance of the focal point of the imaging beam from the distal end of the probe 130 can be determined by the optical element 152. Accordingly, in some instances the focal power of the optical element 152 is selected to have a focus depth corresponding to likely distance of the distal end of the probe 130 from the target biological tissue during use. For example, in some implementations of the probe 130 for retinal imaging, the focal power of the optical element 152 is selected such that the focal point of the imaging beam can be between 1 mm and 20 mm, between 5 mm and 10 mm, between 7 mm and 8 mm, or approximately 7.5 mm beyond the distal end of the probe 130.

Figure 2:
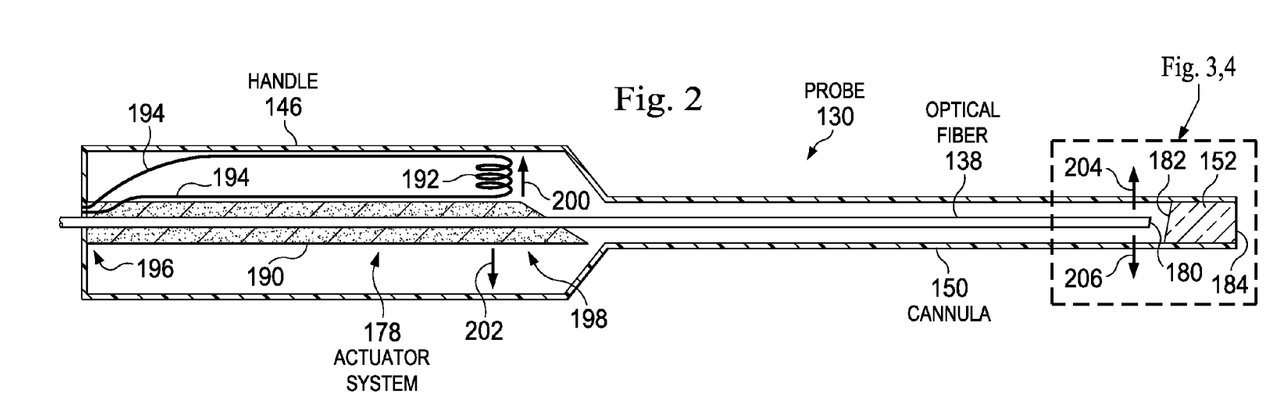
FIG. 2 is a stylized illustration of a cross-sectional view of an imaging probe.

FIG. 2 is a stylized illustration of a cross-sectional view of an embodiment of probe 130 in accordance with an aspect of the present disclosure. As shown, the optical fiber 138 extends along the length of the probe 130 through the handle 146 and the cannula 150. In the illustrated embodiment, an actuator system 178 is positioned within the handle 146. The actuator system 178 is configured to impart motion to the optical fiber 138 such that a distal end 180 of the optical fiber 138 moves with respect to the cannula 150 and optical element 152 that is fixedly secured to the cannula. More specifically, the distal end 180 of the optical fiber 138 can be moved with respect to the optical element 152 to scan the imaging beam across a desired pattern with respect to the target biological tissue.

The optical element 152 is configured to focus the imaging beam received from the optical fiber 138 onto the target biological tissue. In that regard, the optical element 152 includes a proximal face 182 and a distal face 184. The imaging beam enters the optical element 152 through proximal face 182 and leaves the optical element 152 through distal face 184. As shown, the proximal face 182 of the optical element 152 can extend at an oblique angle with respect to the longitudinal axis of the cannula 150. By having the proximal face 182 oriented at an oblique angle, the amount of reflection resulting from the imaging beam entering the optical element 152 can be reduced. In other embodiments, the proximal face 182 extends perpendicular to the longitudinal axis of the cannula 150.

The distal end 180 the optical fiber 138 can be spaced from the proximal face 182 of the optical element 152. In that regard, the spacing between the distal end 180 of the optical fiber 138 and the proximal face 182 of the optical element 152 can be selected to achieve a desired optical performance (e.g., focal distance, focus size, etc.). The spacing between the distal end 180 of the optical fiber 138 and the proximal face 182 of the optical element 152 can also be selected to allow a desired range of motion of the optical fiber 138 within the cannula 150 without physically contacting the optical element 152. The optical element 152 can be mechanically coupled to the distal end 180 of the optical fiber 138 so that the optical element 152 moves with the distal end 180 of the optical fiber 138.

The actuator system 178 is configured to impart motion to the optical fiber 138 such that the distal end 180 of the optical fiber 138 can be moved with respect to the optical element 152 to scan the imaging beam across a desired pattern with respect to the target biological tissue. The actuator system 178 can include a ferrofluid-impregnated medium 190, a coil 192, and electrical conductors 194.

The ferrofluid-impregnated medium 190 can be any suitable ferrofluid-impregnated medium. The medium can be any material capable of absorbing a fluid and/or a slurry containing magnetic solid particles, including without limitation paper, porous medium, absorbing medium, and/or combinations thereof. In some implementations, the medium is a paper that has been soaked with a ferrofluid. The ferrofluid can be composed of a carrier fluid having particles of magnetite, hematite, or other compound containing iron disposed therein. The ferrofluid can include a surfactant (e.g., oleic acid, tetramethylammonium hydroxide, citric acid, soy lecithin, etc.) or not. The ferrofluid can be composed of approximately 85% carrier, 10% surfactant, and 5% magnetic solids. In some particular embodiments, the ferrofluid impregnated medium includes features similar to those described by Ding et al. in "Ferrofluid-Impregnated Paper Actuators," *Journal of Microelectricalmechanical Systems* 20.1 (2011): 59-64, which is hereby incorporated by reference in its entirety. The ferrofluid soaked medium can be coated with one or more layers of parylene or other suitable polymer (e.g., using vapor deposition) to provide a moisture barrier. The polymer coating layer(s) can have a thickness of 10 microns or less, 5 microns or less, or 1 micron or less.

A proximal section 196 of the ferrofluid-impregnated medium 190 is fixedly secured to the housing defining handle 146, while a distal section 198 of the ferrofluid-impregnated medium 190 is movable with respect to the housing. More specifically, the actuator system 178 is configured to cause the ferrofluid-impregnated medium 190 to move with respect to the housing in response to selectively, electrically energizing the coil 192.

For example, by selectively passing current through the coil 192 via electrical conductors 194 a corresponding magnetic field is generated. The resulting magnetic field causes the distal section 198 of the ferrofluid-impregnated medium 190 to either be attracted to the coil 192 or repelled from the coil 192 depending on the characteristics of the generated magnetic field and the ferrofluid-impregnated medium 190. As a result, the distal section 198 of the ferrofluid-impregnated medium 190 is either moved towards the coil 192 (when attracted to the coil 192) as indicated by arrow 200 or away from the coil 192 (when repelled from the coil 192) as indicated by arrow 202. Accordingly, by controlling the amount and/or direction of current passing through the coil 192 via electrical conductors 194, the magnitude and direction of the resulting magnetic field can be controlled to impart a desired motion profile to the ferrofluid-impregnated medium 190.

In some other embodiments, the ferrofluid-impregnated medium 190 and the electrically energizable coil 192 can be positioned in the cannula 150.

A proximal section of the optical fiber 138 can be secured to the ferrofluid-impregnated medium 190 such that the optical fiber 138 moves with the distal section 198 of the ferrofluid-impregnated medium 190 in response to the selective energizing of the coil 192. The proximal section of the optical fiber 138 can be secured to the housing adjacent to the proximal section 196 of the ferrofluid-impregnated medium 190. The proximal section of the optical fiber 138 can be secured to the ferrofluid-impregnated medium 190 using a suitable adhesive (e.g., glue, epoxy, etc.), mechanical connection, and/or combinations thereof.

As shown, the optical fiber 138 is secured to the ferrofluid-impregnated medium 190 such that the distal end 180 of the optical fiber 138 extends distally beyond the distal section 198 of the ferrofluid-impregnated medium 190. In this manner, the distal end 180 of the optical fiber 138 is cantilevered from the ferrofluid-impregnated medium 190. As a result, the motion profile of the distal end 180 of the optical fiber 138 is amplified relative to the motion profile of the distal section 198 of the ferrofluid-impregnated medium 190. In other words, the movement of the distal end 180 of the optical fiber 138 is greater than the corresponding movement of the distal section 198 of the ferrofluid-impregnated medium 190 that is caused by the selective energizing of coil 192. For example, when the distal section 198 of the ferrofluid-impregnated medium 190 is moved towards the coil 192 (when attracted to the coil 192) as indicated by arrow 200, the distal end 180 of the optical fiber will move as indicated by arrow 204 a greater distance in the same direction. Similarly, when the distal section 198 of the ferrofluid-impregnated medium 190 is moved away from the coil 192 (when repelled from the coil 192) as indicated by arrow 202, the distal end 180 of the optical fiber will move as indicated by arrow 206 a greater distance in the same direction. The ratio of the movement of the distal end 180 of the optical fiber 138 to the movement of the distal section 198 of the ferrofluid-impregnated medium 190 can be between 1.01:1.0 and 10.0:1.0, between 1.1:1.0 and 5.0:1.0, or between 1.5:1.0 and 2.0:1.0. Accordingly, the resultant movement of the distal end 180 of the optical fiber 138 can be more than 1%, 10%, 20%, 50%, 100%, 500%, or 1000% greater than the movement of the distal section 198 of the ferrofluid-impregnated medium 190.

In some instances, the motion profile of the distal end 180 of the optical fiber simulates a lever arm action with a pivot point within the handle 146 of the probe 130. For example, the pivot point can be defined by the connection of the proximal section of the optical fiber 138 and/or the proximal section 196 of the ferrofluid-impregnated medium 190 to the housing defining the handle 146. In some instances, the ferrofluid-impregnated medium 190 can maintain a planar orientation during movement. In other instances, the ferrofluid-impregnated medium 190 bends during movement such that at least a portion of the ferrofluid-impregnated medium 190 has an arcuate shape. For example, in some instances the distal section 198 of the ferrofluid-impregnated medium 190 bends relative to the fixed proximal section 196 during movement caused by electrically activating the coil 192.

Figure 3:
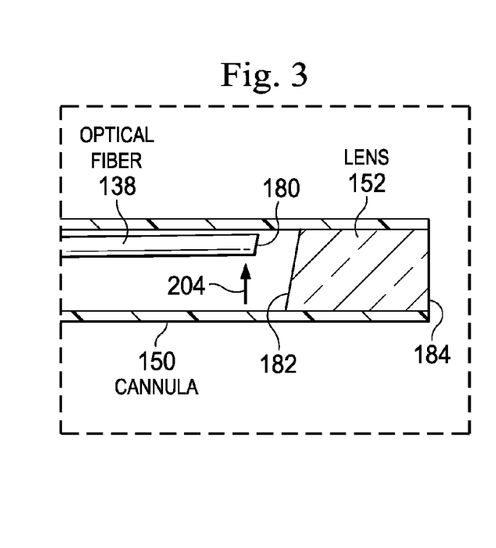
FIG. 3 is a stylized illustration of a cross-sectional view of a distal portion of the imaging probe of FIG. 2 showing an optical fiber of the imaging probe in a first position in accordance with an aspect of the present disclosure.
Figure 4:
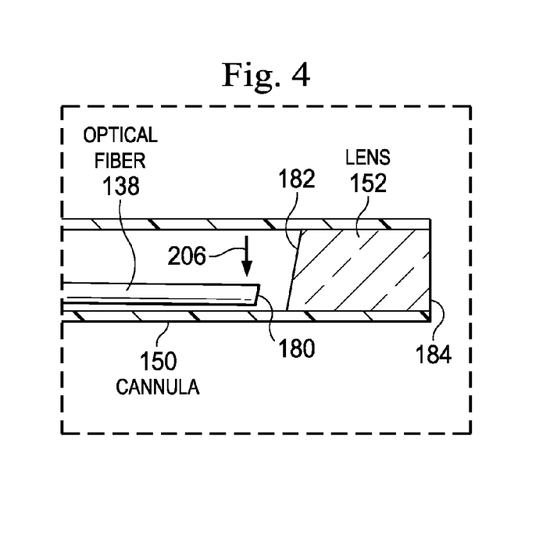
FIG. 4 is a stylized illustration of a cross-sectional view of the distal portion of the imaging probe of FIG. 2, similar to that of FIG. 3, but showing the optical fiber in a second position in accordance with an aspect of the present disclosure.
Figure 5:
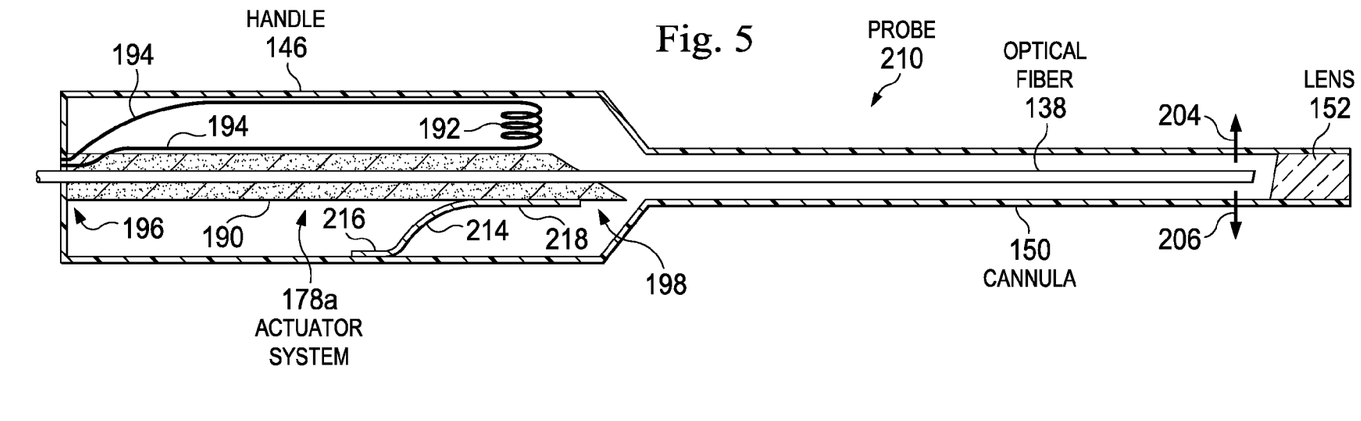
FIG. 5 is a stylized illustration of a cross-sectional view of an imaging probe.

Generally, the actuator system 178 is configured to move the ferrofluid-impregnated medium 190 from a neutral position to one or more activated positions. As a result, the actuator system 178 is likewise configured to move the distal end 180 of the optical fiber 138 from a neutral position to one or more activated positions. For example, FIG. 3 illustrates an embodiment where the neutral position of the optical fiber 138 is coaxial with the longitudinal axis of the cannula 150. The actuator system 178 is configured to move the distal section 198 of the ferrofluid-impregnated medium 190 and, thereby, the distal end 180 of the optical fiber 138 from the position coaxial with the longitudinal axis to a first activated position closer to the coil 192 (as depicted in FIG. 4) and a second activated position further away from the coil 192 (as depicted in FIG. 5). Current can flow through the coil 192 in a first direction to urge the ferrofluid-impregnated medium 190 and, thereby, the distal end 180 of the optical fiber 138 towards the first activated position and flow through the coil 192 in a second direction, opposite the first direction, to urge the ferrofluid-impregnated medium 190 and, thereby, the distal end 180 of the optical fiber 138 towards the second activated position.

By oscillating the optical fiber between the first and second activated positions illustrated in FIGS. 3 and 4, the imaging beam can be scanned across the target biological tissue, such as the retina. In some implementations, the actuator system 178 is configured to oscillate the distal end 180 of the optical fiber 138 between the first and second activated positions within a frequency range between about 1 Hz and about 30 Hz, although other frequency ranges, both larger and smaller, are contemplated.

The positions of the distal end 180 of the optical fiber 138 depicted in FIGS. 3 and 4 can also be the neutral position for the actuator system 178. In that regard, the distal end 180 of the optical fiber 138 begins in the position of FIG. 3 or FIG. 4 and then moves to the position of FIG. 4 or FIG. 3, respectively, upon of the coil 192 being energized. In such implementations, current can flow through the coil 192 in a manner to urge the ferrofluid-impregnated medium 190 and, thereby, the distal end 180 of the optical fiber 138 towards the opposite position. By stopping the current and/or reversing the current, the ferrofluid-impregnated medium 190 and the distal end 180 of the optical fiber 138 are urged back towards the starting position. As discussed below, in some implementations the actuator system 178 can include one or more restoring elements to facilitate returning the ferrofluid-impregnated medium 190 and the optical fiber 138 back to the starting, neutral position. The restoring element(s) can be mechanical and/or electromagnetic.

FIG. 5 is a stylized illustration of a cross-sectional view of an imaging probe 210 in accordance with another aspect of the present disclosure. Probe 210 includes many features similar to those discussed above with respect to probe 130 that will not be repeated here for sake of brevity. Probe 210 includes an actuator system 178a. The actuator system 178a is configured to impart motion to the optical fiber 138 such that the distal end 180 of the optical fiber 138 can be moved with respect to the optical element 152 to scan the imaging beam across a desired pattern with respect to the target biological tissue. The actuator system 178a can include a ferrofluid-impregnated medium 190, a coil 192, electrical conductors 194, and a restoring element 214. The restoring element 214 is configured to urge the ferrofluid-impregnated medium 190 and, thereby, the optical fiber 138 back to a starting position. The starting position can be a position similar to the positions shown in any of FIGS. 2-4.

In the illustrated embodiment of FIG. 5, the restoring element 214 is a leaf spring. In that regard, a proximal section 216 of the restoring element 214 is fixedly secured to the housing defining handle 146, while a distal section 218 of restoring element 214 is configured to interface with the distal section 198 of the ferrofluid-impregnated medium 190. In particular, as the distal section of the ferrofluid-impregnated medium 190 is displaced by energizing the coil 192 the distal section 218 of the restoring element 214 will be correspondingly displaced. When the coil 192 is no longer energized (or the current through the coil 192 is reversed) the potential energy resulting from displacement of the distal section 218 of the flexible restoring element 214 will impart a restoring force on the ferrofluid-impregnated medium 190 to cause it to return to its starting position.

Figure 6:
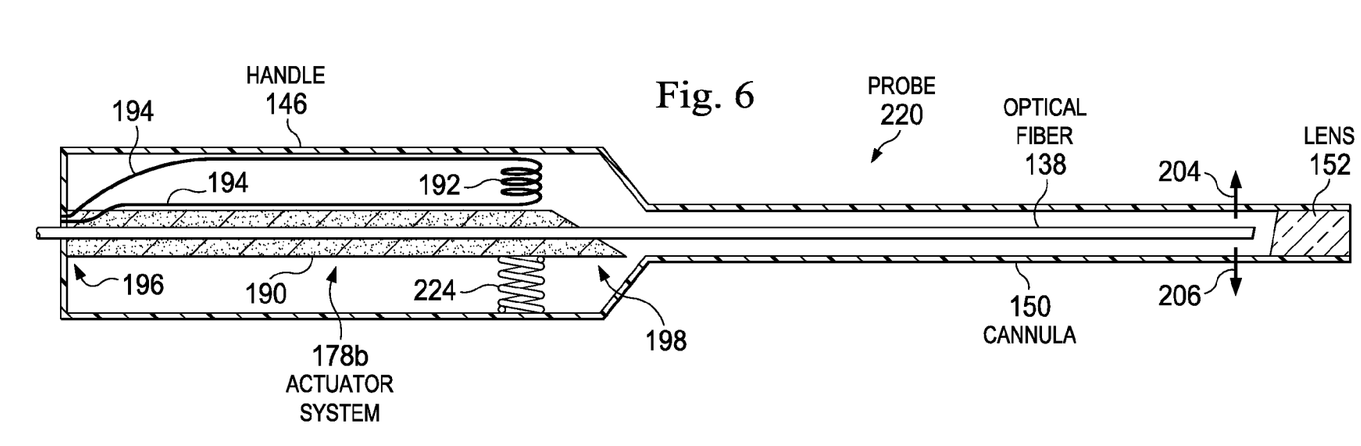
FIG. 6 is a stylized illustration of a cross-sectional view of an imaging probe.

FIG. 6 is a stylized illustration of a cross-sectional view of an imaging probe 220 in accordance with another aspect of the present disclosure. Probe 220 includes many features similar to those discussed above with respect to probes 130 and 210 that will not be repeated here for sake of brevity. Probe 220 includes an actuator system 178b. Actuator system 178b is similar to actuator system 178a of probe 210, but includes an alternative restoring element. In the illustrated embodiment of FIG. 6, the actuator system 178b includes a restoring element 224 that is a coil spring. In that regard, a lower portion of the coil spring is fixedly secured to the housing defining handle 146, while an upper portion of the coil spring is configured to interface with the distal section 198 of the ferrofluid-impregnated medium 190. In particular, as the distal section of the ferrofluid-impregnated medium 190 is displaced by energizing the coil 192 the coil spring will be correspondingly compressed. When the coil 192 is no longer energized (or the current through the coil 192 is reversed) the potential energy resulting from compression of the flexible restoring element 224 will impart a restoring force on the ferrofluid-impregnated medium 190 to cause it to return to its starting position.

Figure 7:
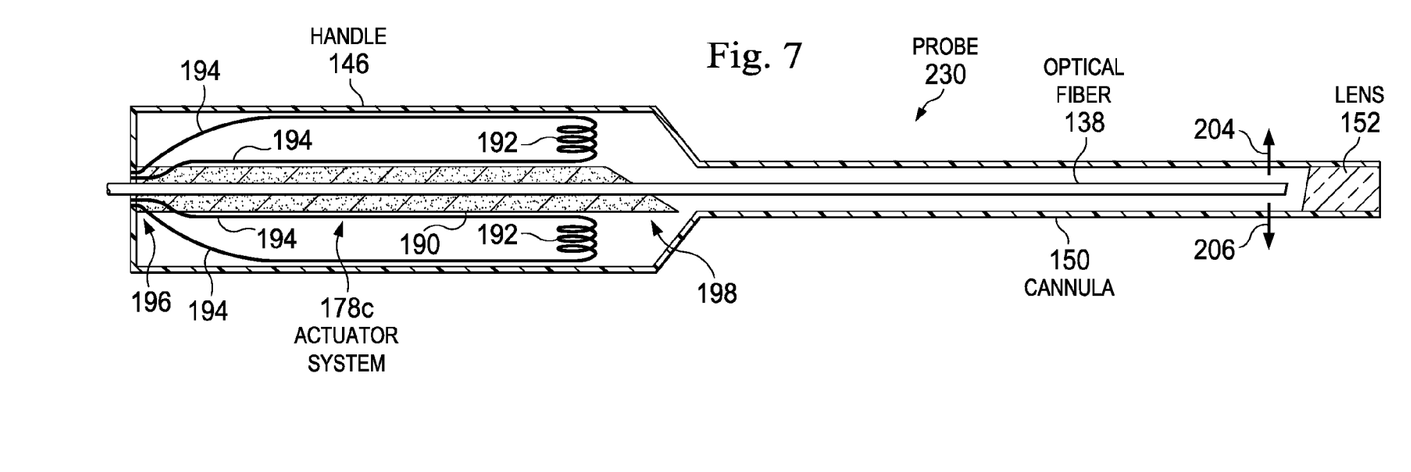
FIG. 7 is a stylized illustration of a cross-sectional view of an imaging probe.

FIG. 7 is a stylized illustration of a cross-sectional view of an imaging probe 230 in accordance with another aspect of the present disclosure. Probe 230 includes many features similar to those discussed above with respect to probes 130, 210, and 220 that will not be repeated here for sake of brevity. Probe 230 includes an actuator system 178c. In the illustrated embodiment of FIG. 7, the actuator system 178c includes a coil 192 and electrical conductors 194 on each side of the ferrofluid-impregnated medium 190. In that regard, by having a coil 192 on each side of the ferrofluid-impregnated medium 190, the coils can be selectively activated to urge the ferrofluid-impregnated medium 190 towards or away from a particular coil to impart corresponding motion to the optical fiber 138. The opposing coils 192 may be energized in an alternating pattern (i.e., only one coil energized at a time) or the opposing coils 192 may be energized simultaneously in a coordinated manner (e.g., having current flow through each of the coils 192 simultaneously, but in a manner that urges the ferrofluid-impregnated medium 190 in a common direction, which may require the current to flow in the same or opposite directions depending on the arrangement). By selectively controlling the current flowing through the opposing coils 192, the relative position of the ferrofluid-impregnated medium 190 to starting and activated positions can be controlled.

Figure 8:
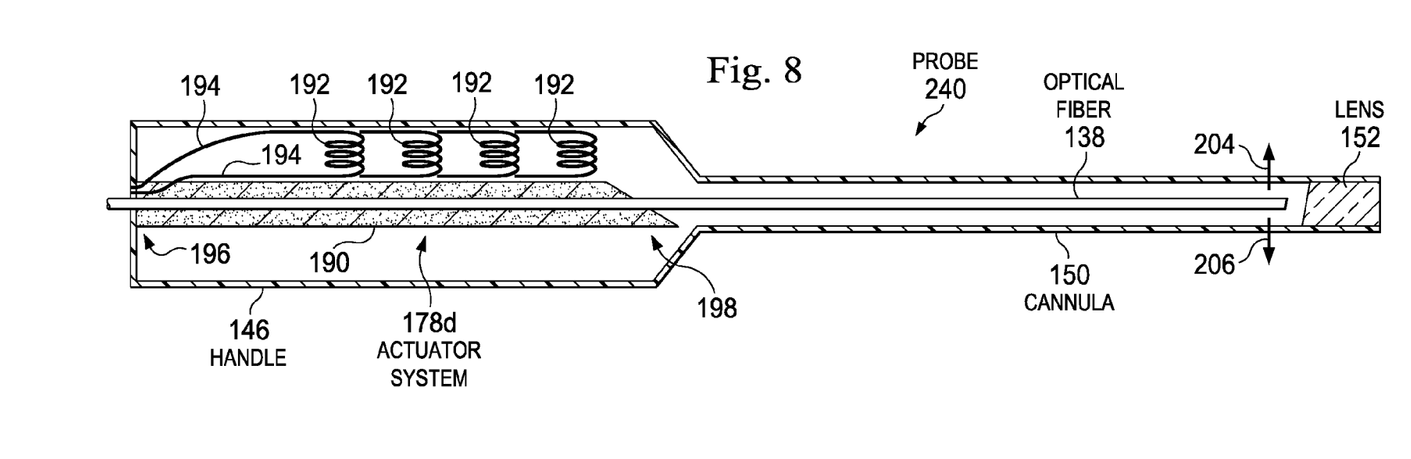
FIG. 8 is a stylized illustration of a cross-sectional view of an imaging probe.

FIG. 8 is a stylized illustration of a cross-sectional view of an imaging probe 240 in accordance with another aspect of the present disclosure. Probe 240 includes many features similar to those discussed above with respect to probes 130, 210, 220, and 230 that will not be repeated here for sake of brevity. Probe 240 includes an actuator system 178d. Actuator system 178d is similar to actuator system 178 of probe 130, but includes multiple coils 192. In the illustrated embodiment, the actuator system 178d includes four coils 192 arranged in a linear pattern along the length of the ferrofluid-impregnated medium 190. However, it is understood that virtually any number of coils 192, including two or more, may be utilized. Further, it is understood that the coils 192 may be arranged in virtually any type of two-dimensional or three-dimensional configuration relative to the ferrofluid-impregnated medium 190, including without limitation symmetrical, non-symmetrical, geometric, and non-geometric patterns. In some instances, a larger number of coils 192 are positioned adjacent the distal section 198 of the ferrofluid-impregnated medium 190 than the proximal section 196. The coils 192 may be wired in series, parallel, as individual circuits (i.e., each with dedicated electrical conductors 194), and/or combinations thereof.

Figure 9:
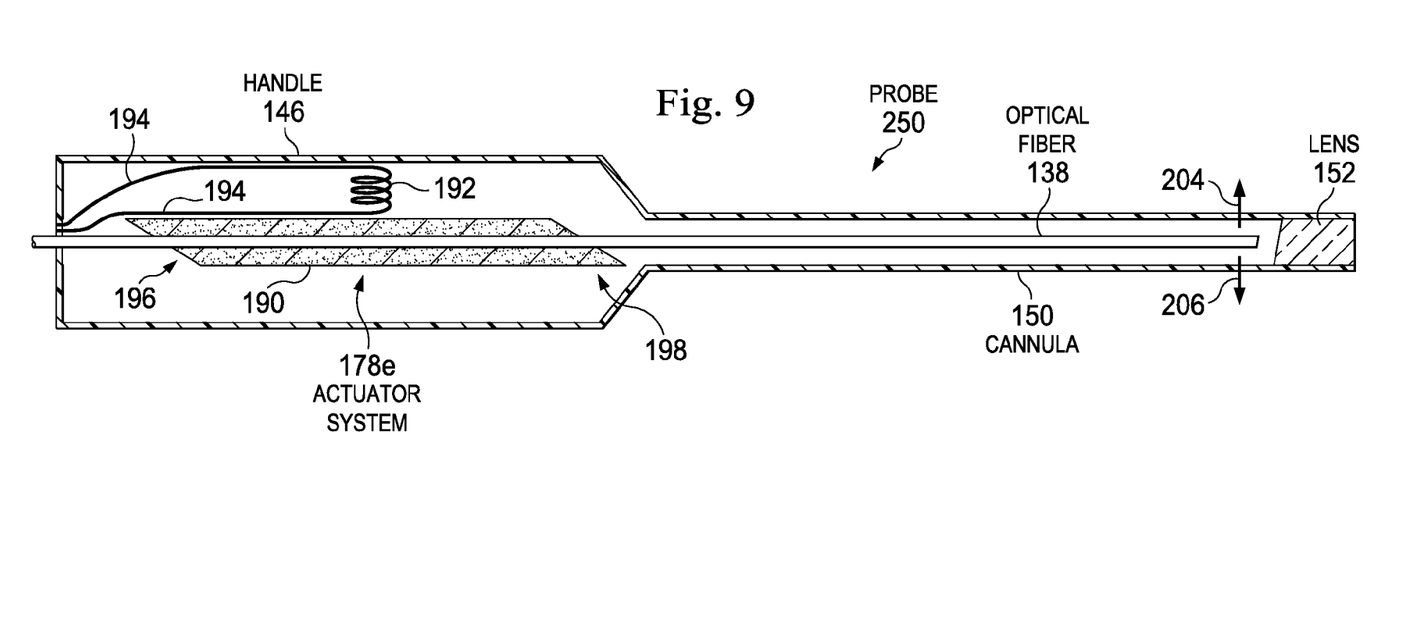
FIG. 9 is a stylized illustration of a cross-sectional view of an imaging probe.

FIG. 9 is a stylized illustration of a cross-sectional view of an imaging probe 250 in accordance with another aspect of the present disclosure. Probe 250 includes many features similar to those discussed above with respect to probes 130, 210, 220, 230, and 240 that will not be repeated here for sake of brevity. Probe 250 includes an actuator system 178e. Actuator system 178e is similar to actuator system 178 of probe 130, except that the proximal section 196 of the ferrofluid-impregnated medium 190 is not secured to the housing defining handle 146. Instead, other than being coupled to optical fiber 138, the ferrofluid-impregnated medium 190 is free from attachments. The proximal section of the optical fiber 138 can be secured to the housing defining handle 146. Without being secured to the housing, the ferrofluid-impregnated medium 190 can have an increased range of motion in response to the selective energizing of the coil 192.

The motion profiles discussed in the context of the actuator systems above focused on linear displacement of the optical fiber 138 within cannula, which can be utilized to produce a corresponding linear scan of the imaging beam across the target biological tissue. In other embodiments, the actuator system 178 can include two ferrofluid-impregnated media 190, oriented perpendicular to one another with corresponding coils 192 that can be selectively energized to scan the optical fiber 138 and the imaging beam across a two-dimensional scanning pattern. One of the two ferrofluid-impregnated media 190 can be configured to impart motion to the optical fiber 138 along a first axis and the other of the two ferrofluid-impregnated media 190 can be configured to impart motion to the optical fiber 138 along a second axis perpendicular to the first axis. The two-dimensional scanning pattern can include a spiral, a raster, a constant-radius asterisk, a multiple-radius asterisk, a multiply folded path, other two-dimensional scan patterns, and/or combinations thereof.

In yet other embodiments, the actuator system 178 can include more than two FIMs 190, with corresponding coils 192. These FIMs 190 can impart motion to the optical fiber 138 along corresponding axes.

Some embodiments include the ophthalmic imaging system 120 to generate an imaging light, comprising an imaging light source 122, configured to generate an imaging light; and the probe 130 that includes the handle 146, sized and shaped for handheld grasping by a user; the cannula 150, coupled to the handle 146, the cannula 150 sized and shaped for insertion into an eye to be treated; the optical fiber 138 being positioned partially within the probe 130, in optical communication with the imaging light source 122 to guide the imaging light to the optical element 152 positioned in a distal region of the cannula 150; and the actuator system 178 configured to impart motion to the optical fiber 138, the actuator system 178 including a ferrofluid-impregnated medium (FIM) 190 and an electrically energizable coil 192, positioned within the probe 130.

Embodiments as described herein may provide an imaging probe having an actuator that utilizes a ferrofluid-impregnated medium to impart motion to an optical fiber positioned within the imaging probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic imaging apparatus, comprising:
an optical probe having:
a handle sized and shaped for handheld grasping by a user;
a cannula coupled to the handle, the cannula sized and shaped for insertion into an eye to be treated, and the cannula being substantially hollow; and
an optical element positioned within the cannula;
an optical fiber positioned within the handle of the optical probe and extending into the cannula of the optical probe, the optical fiber configured to receive an imaging light from an imaging light source and guide the imaging light to the optical element; and
an actuator system configured to impart motion to the optical fiber without the actuator system extending into the cannula of the optical probe, the actuator system including a ferrofluid-impregnated medium (FIM) and an electrically energizable coil positioned within the handle of the optical probe, wherein a first portion of FIM is coupled to the handle and a second portion of the FIM is coupled to the optical fiber such that actuator system is configured to move the optical fiber relative to the handle, and wherein the optical fiber is coupled to the FIM within the handle of the optical probe so that a distal end of the optical fiber extends past a distal end of the FIM and into the substantially hollow cannula of the optical probe such that motion imparted to the distal end of the optical fiber is amplified relative to movement of the FIM.

2. The ophthalmic imaging apparatus of claim 1, wherein:
a distal section of the FIM is spaced from the handle and configured to move relative to the handle in response to the electrically energizable coil being electrically energized.

3. The ophthalmic imaging apparatus of claim 2, wherein a proximal section of the FIM is affixed to the handle.

4. The ophthalmic imaging apparatus of claim 1, wherein:
a proximal section of the optical fiber is affixed to the handle.

5. The ophthalmic imaging apparatus of claim 1, wherein the optical probe further comprises:
a connector configured to be removably coupled to a connector associated with the imaging light source such that the optical probe is disposable.

6. The ophthalmic imaging apparatus of claim 1, wherein the FIM comprises:
at least one of a paper, a porous medium, and an absorbing medium.

7. The ophthalmic imaging apparatus of claim 1, wherein:
the actuator system further includes a restoring element configured to counteract the motion imparted to the optical fiber by the electrically energizable coil being electrically energized.

8. The ophthalmic imaging apparatus of claim 7, wherein:
the restoring element is a flexible restoring element.

9. The ophthalmic imaging apparatus of claim 7, wherein:
the restoring element is a further electrically energizable coil.

10. The ophthalmic imaging apparatus of claim 1, wherein:
the optical element comprises at least one of a lens and a gradient index (GRIN) lens.

11. The ophthalmic imaging apparatus of claim 1, wherein:
the optical element is mechanically coupled to a distal end of the optical fiber so that the optical element moves with the distal end of the optical fiber.

12. The ophthalmic imaging apparatus of claim 1, wherein:
the actuator system comprises one or more additional FIM and one or more additional electrically energizable coil, wherein
the FIM is configured to impart motion to the optical fiber along a first axis and the additional FIM is configured to impart motion to the optical fiber along an additional axis different from the first axis.

13. An ophthalmic imaging system, comprising:
an imaging light source, configured to generate an imaging light; and
a probe for gathering image data, including:
a handle, sized and shaped for handheld grasping by a user;
a substantially hollow cannula, coupled to the handle, the cannula sized and shaped for insertion into an eye to be treated;
an optical element positioned in a distal region of the cannula;
an optical fiber,
positioned partially within the probe and extending into the cannula of the probe,
in optical communication with the imaging light source to guide the imaging light to the optical element; and
an actuator system configured to impart motion to the optical fiber without the actuator system extending into the cannula of the probe, the actuator system including a ferrofluid-impregnated medium (FIM) and an electrically energizable coil positioned within the probe, wherein a first portion of FIM is coupled to the handle and a second portion of the FIM is coupled to the optical fiber such that actuator system is configured to move the optical fiber relative to the handle, and wherein the optical fiber is coupled to the FIM within the handle of the optical probe so that a distal end of the optical fiber extends past a distal end of the FIM and into the substantially hollow cannula of the optical probe such that motion imparted to the distal end of the optical fiber is amplified relative to movement of the FIM.

14. The ophthalmic imaging system of claim 13, further comprising:
a controller in communication with the light source, the controller configured to control actuation of the imaging light source for an optical coherence tomography (OCT) imaging procedure.

15. The ophthalmic imaging system of claim 14, wherein:
the controller is configured to control the actuation system to impart motion to the optical fiber to scan the imaging light along a scanning pattern with a linear extent between 1 mm and 5 mm at a distance between 5 mm and 10 mm from a distal end of the optical probe.

16. The ophthalmic imaging system of claim 14, wherein:
the controller is configured to control the actuator system to impart motion to the optical fiber to scan the imaging light over a two-dimensional scanning pattern.

17. The ophthalmic imaging system of claim 16, wherein:
the two dimensional scanning pattern comprises at least one of a spiral, a raster, a constant-radius asterisk pattern, a multiple-radius asterisk pattern, and a multiply folded path.

18. The ophthalmic imaging system of claim 14, further comprising:
a display in communication with the controller, wherein the controller is further configured to process the image data obtained by the probe and output imaging data to the display.

* * * * *